United States Patent
Ross et al.

[11] Patent Number: 5,254,857
[45] Date of Patent: Oct. 19, 1993

[54] FAST SCANNING ELECTRON MICROSCOPE (FSEM)

[75] Inventors: Timothy J. Ross; Ming L. Wang, both of Albuquerque, N. Mex.; Ian D. R. Mackinnon, Middle Park, Australia

[73] Assignee: Kachina Technologies, Inc., Albuquerque, N. Mex.

[21] Appl. No.: 963,038

[22] Filed: Oct. 19, 1992

Related U.S. Application Data

[63] Continuation of Ser. No. 708,505, May 31, 1991, abandoned.

[51] Int. Cl.$^5$ .............................................. H01J 37/28
[52] U.S. Cl. ................................. 250/310; 250/396 ML
[58] Field of Search .......... 250/310, 311, 397, 396 R, 250/396 ML; 335/210, 213; 73/826, 834

[56] References Cited

U.S. PATENT DOCUMENTS

| | | | |
|---|---|---|---|
| 3,671,743 | 6/1972 | Nixon | 250/310 |
| 4,180,738 | 12/1979 | Smith et al. | 250/310 |
| 4,434,371 | 2/1984 | Knauer | 250/396 R |
| 4,476,386 | 10/1984 | Reid et al. | 250/310 |
| 4,713,687 | 12/1987 | Shimizu et al. | 250/310 |
| 4,789,781 | 12/1988 | Kitagawa et al. | 250/310 |

Primary Examiner—Jack I. Berman
Attorney, Agent, or Firm—Samuel M. Freund

[57] ABSTRACT

High magnification and large depth of field with a temporal resolution of less than 100 microseconds are possible using the present invention which combines a linear electron beam produced by a tungsten filament from an SX-40A Scanning Electron Microscope (SEM), a magnetic deflection coil with lower inductance resulting from reducing the number of turns of the saddle-coil wires, while increasing the diameter of the wires, a fast scintillator, photomultiplier tube, photomultiplier tube base, and signal amplifiers and a high speed data acquisition system which allows for a scan rate of 381 frames per second and 256×128 pixel density in the SEM image at a data acquisition rate of 25 MHz. The data acquisition and scan position are fully coordinated. A digitizer and a digital waveform generator which generates the sweep signals to the scan coils run off the same clock to acquire the signal in real-time.

11 Claims, 7 Drawing Sheets

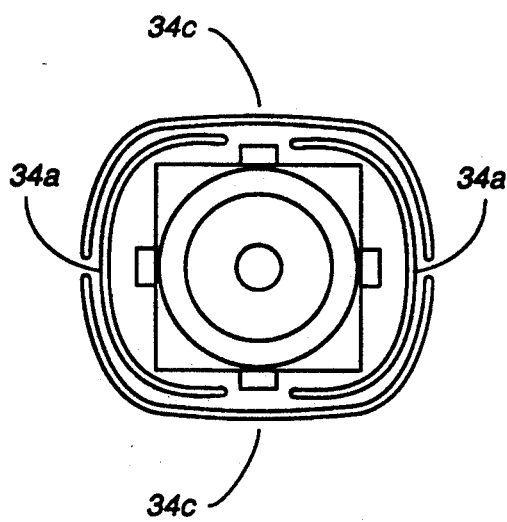
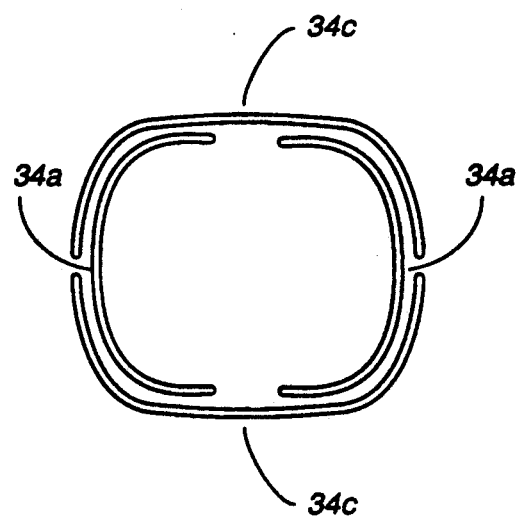
Fig. 3b  Fig. 3c

FAST SCANNING ELECTRON MICROSCOPE (FSEM)

This is a continuation of copending application Ser. No. 07/708,505 filed on May 31, 1992, now abandoned.

BACKGROUND OF THE INVENTION

The present invention relates generally to scanning electron microscopes (SEMs), and more particularly to a fast scanning electron microscope (FSEM) capable of greater than 1 KHz framing rate with a large depth of focus and submicron resolution.

Light microscopes offering less than 2 micron spatial resolution and 25 nanosecond temporal resolution in strobed mode (2 kHz maximum real-time framing rate) have recently been developed (See, e.g., A. Ogura, N. Aizaki, and H. Terao, in "High-Speed Video Observation of Laser Recrystallization for Semiconductor-on-Insulator Fabrication," J. Appl. Phys. 65, 752 (1988).). However, transmission (TEM), reflection (REM) and scanning electron microscopes (SEM) offer spatial resolution superior to that of light microscopes. Transmission and reflection electron microscopes also provide temporal resolution of about 20 nanoseconds/frame, rivaling the temporal resolution of light microscopes. SEM, however, is the only type of electron microscope which offers both high spatial resolution and large depth of focus surface imaging, even for rough surfaces, of particular value for surface studies of material responses to dynamic loads at high magnifications, for example.

Recent advances in high-speed electron microscopy have used single-shot, microchannel-plate enhancement of light images obtained with transmission or reflection electron microscopes (See, e.g., O. Bostanjoglo, "Electron Microscopy of Fast Processes," Adv. Electron. Physics 76, 209 (1989).). Time resolution of about 20 nanoseconds is typical in these experiments. TEM, however, cannot image surfaces (except for monolayers), and requires thin specimens transparent, more or less, to electrons at the TEM operating voltage. Reflection electron microscopy offers surface imaging of sufficiently smooth surfaces but often presents greatly foreshortened images and depth of focus inferior to that of SEM.

As for temporal resolution in dynamic microscopy, Bostanjoglo [1989] has used pulsed-laser cathodes in TEM and the reflection electron microscope to attain temporal resolution of 20 nanoseconds. However, these experiments require the use of micro-channel plate intensified light images and are generally restricted to single-frame images inadequate to assess dynamic response. In addition, specimen beam damage is a consideration at the illumination levels required to produce usable images in such short illumination times. SEM framing rates are typically 1 Hz or less for atomic-scale scans due, primarily, to limited electro-mechanical scan bandwidth and extremely low imaging currents (higher currents would destroy the specimen). Rates of greater than 100 Hz are possible for SEM at lower magnifications. J. J. Wendolosky, K. H. Gardner, J. Hirschinger, H. Miura, and A. D. English, in "Molecular Dynamics in Ordered Structures: Computer Simulation and Experimental Results for Nylon 66 Crystals," Science 247, 431 (1990), quote NMR spectroscopy temporal resolution of 10 picoseconds. A. Ogura, N. Aizaki, and H. Terao, in "High-Speed Video Observation of Laser Recrystallization for Semiconductor-on-Insulator Fabrication," J. Appl. Phys. 65, 752 (1988), use a high-speed Kodak video recording system (1 kHz framing rate for full-frame, higher for partial frames) and laser illumination to obtain fast conventional light dynamic microscopy. A variety of real-time experiments with TEM and SEM has been performed at TV framing rates (30–50 Hz). Professor Kulabek (L. J. Balk, University of Duisberg, West Germany, written communication, Jan. 23, 1990.) has operated a secondary electron detector in a real-time SEM at a 16 MHz signal acquisition rate (about 5 times TV-rate). Also, strobed operation of SEM and the Auger microprobe permit less than 1 nanosecond temporal resolution, but only for cyclic phenomena. In strobed operation, Ogura cites temporal resolution of 25 nanoseconds using a pulsed laser illumination source.

Strobed SEM operation is well-suited to measuring integrated circuit potentials (using voltage contrast" techniques) when the circuit is operated cyclically, which is common for digital circuitry. It may also be possible to obtain very high-quality, short temporal resolution, strobed SEM images for material science studies by cyclic mechanical loading using, for example, sonic or ultrasonic propagation of either volume or surface waves in specimens of interest.

There is one other microscope (See, e.g., G. S. Kino and T. R. Corle, "Confocal Scanning Optical Microscopy," Physics Today, September, 1989, p. 55.) that is of interest in dynamic microscopy. This microscope is a "video-rate" confocal scanning light microscope. It has the potential for framing rates comparable to the lower end of our FSEM framing rates, with the spatial resolution of about 5000 Angstroms typical of conventional light microscopes but with superior sharpness due to improved edge resolution. In this device, fast laser beam scanning is obtained with acoustic-optic deflection capable of 200 MHz bandwidth (See, e.g., A. Yariv and P. Yeh, *Optical Waves in Crystal*, p. 383, Wiley and Sons, 1985.). The imaging signal is obtained with a scanned image dissector tube capable of 20 MHz signal acquisition rate and 0.5 MHz deflection bandwidth (See, e.g., S. Goldstein, "A No-Moving Parts Video Rate Laser Beam Scanning Type 2 Confocal Reflected/Transmission Microscope," J. Micros. 153, RP1 (1989).).

However, at higher loading rates (often single-pulse), hysteretic effects or catastrophic events such as brittle fracture or other sorts of material failure will require the use of a real-time, non-strobed, dynamic scanning electron microscope such as our FSEM. Because the scan beam in the SEM is an electron beam, maximum deflection rates typical of electrostatically-deflected oscilloscopes, permitting signal acquisition rates of approximately 10 GHz, allow for the potential of FSEM framing rates approaching 1 MHz.

As shown in FIG. 1, fast scanning for time-resolved electron microscopy (EM) in the prior art has only been conducted in a pulse-mode (non-continuous) on conventional (non-scanning) electron microscopes, and only stroboscopic imaging (periodic imaging) has been conducted on scanning electron microscopes (SEM).

ADVANTAGES OF OUR FAST SCANNING ELECTRON MICROSCOPE (FSEM)

FSEM has the potential for spatial resolution two orders of magnitude better than light microscopes, real-time framing rate close to three orders of magnitude better than light microscopes, and the advantage of large depth of focus which is important even at low magnifications, particularly for dynamic processes in which the region under observation moves along the microscope optical axis.

FSEM also does not have the problems associated with conventional electron microscopy, though it has limitations in temporal resolution and, for digital acquisition, in relative spatial resolution (pixel resolution). With our present FSEM system we project that we can image at perhaps 20 microseconds per frame at 64 pixels × 64 pixels per frame and, with state-of-the-art components, offer the promise of 2 microseconds per frame at this pixel resolution.

Increasing framing rate by $10^1$–$10^4$ times that presently available (so-called TV-rate-30–50 Hz) permits a variety of new dynamic microscopy studies. SEM also permits measurement of surface electrostatic potentials (voltage changes as low as 0.5 millivolts have been measured (See, e.g., A. Gopinath, Adv. Electron. Electron Physics 69, 1 (1987).) and magnetic fields (See, e.g., L. Reimer, *Scanning Electron Microscopy*, Sec. 6.3, Springer, Berlin (1985).) permitting submicron mapping of voltages or magnetic field lines on integrated circuits or for observing flux lattice processes in high temperature ($T_c$) superconductors (See, e.g., P. L. Gammel, D. J. Bishop, G. J. Dolan, J. R. Kwo, C. A. Murray, L. F. Schneemeyer, and J. V. Waszczak, Phys. Rev. Lett. 58, 2592 (1987).)

SUMMARY OF THE INVENTION

To obtain high-imaging speed operation in our FSEM, our objective was to address four areas: illumination, detection, deflection and recording. The specimen must be illuminated with an electron beam of sufficient intensity to provide a detectable signal of sufficient quality to provide a good image of the specimen. And, such an image must be obtained at framing speeds of interest with scan beam deflection providing suitable speed and proper deflection waveform, without degrading scan beam quality. The fourth task is to record the imaging signal synchronously with the scan for later playback in a "movie" format. To address these four problems and to illustrate the FSEM technology, we modified a commercially available SX-40A SEM manufactured by International Scientific Instruments, Inc. The unmodified SEM had a tungsten hairpin cathode electron gun, two stages of condenser optics, two-stage magnetic deflection and an objective lens. The invention was reduced to practice through a variety of dynamic tests including the imaging of dynamic fracture in a specimen induced by an in-situ shock device of our own design.

Illumination and detection are related. If the detector detects all imaging radiation produced by the scan beam without introducing noise or frequency errors, further image quality improvements can only be had by increasing illumination. Illumination ultimately determines obtainable image quality. In the case of secondary electron imaging, for example, and typical scan beam (primary electron) energies, one secondary electron is produced for every 1 to 10 primary electrons. Clearly, improving primary beam current can dramatically improve image quality.

The other major problem area we have encountered in obtaining high-imaging speed SEM operation is in deflection of the scan beam at high rates with minimal distortion of the desired deflection waveform (nonlinearity) or degradation of scan beam quality (deflection aberrations). Several improvements to scan generator/scan coil driver electronics were performed. Problems due to the quiescent state of the scan generator producing a constant direct-current input to the scan coil drivers between scans, resulting in image shift and unnecessary power dissipation in the scan coil drivers and scan coil termination resistors have been resolved. Lower magnification was required to properly center specimens in the microscope field of view for dynamic imaging, but the lower magnification requires higher deflection currents causing significant heating in the scan coil termination resistors. These problems were also resolved. Another modification which makes the microscope easier to use is a switch box permitting simple switching between analog data acquisition and digital data acquisition. The specimen is first positioned in the microscope field of view in analog mode, then switched to digital mode to take a digital movie.

The imaging signal output is input to a digital data acquisition system, which consists of a fast digitizer, a digitizer controller (via a GPIB bus), fast memory modules and a chassis containing appropriate power supplies. The digitizer we are using at present is the LeCroy 8828D, capable of a 200 MHz digitizing rate, 8-bit measurement and 1-Mbyte of fast memory storage (expandable to 2 Mbyte). At 256 pixels × 128 pixels per frame this allows for storage of 16 frames of data. The digitizer also provides a clock pulse used to generate scan deflection signals so that data-taking and scanning are synchronized.

DETAILED DESCRIPTION OF THE INVENTION

A commercially available SX-40A SEM manufactured by International Scientific Instruments (ISI) was modified. The unmodified SEM has a tungsten hairpin cathode electron gun, two stages of condenser optics, two-stage magnetic deflection and an objective lens. We replaced the deflection circuitry and coils with ones of our own design to increase deflection speed while preserving the deflection field geometry of the unmodified, in order to preserve the spatial resolution of the original instrument. Alternative approaches involving, for example, electrostatic deflection, would have required extensive computer simulation of the optical/deflection train (See, e.g., H. C. Chu and E. Munro, Optik 61, 121 (1982). To match a new deflection scheme to the existing SEM optics and still retain spatial resolution of greater than 100 nanometers (See e.g., D. S. Alles et al., J. Vac. Sci. Technol. B5, 47 (1987). Spatial resolution closer to the nominal 6 nanometer of the unmodified instrument is attainable. A special detector was built for high-speed secondary electron imaging.

We generate deflection signals and acquire data in two different ways. In the analog mode, ordinary waveform generators provide deflection signals, and imaging data is acquired on a Tektronix 7704 oscilloscope using its z-axis modulation feature to provide contrast imaging. This real-time method is used to focus images and to observe effects of changes in operation parameters. A digital mode is used to record fast dynamic events. In the digital mode, the imaging signal is stored in the fast 1-Mbyte memory of a LeCroy TR8828D digitizer capable of 200 MHz digitizing rate and 8-bit sampling. Scan signals are generated in digital mode directly from the digitizer clock pulse. Acquired data is then retrieved from the fast memory and transferred to a personal computer with at least at 6 MHz clock speed for image processing and display.

Signal-to-noise ratio (S/N) of the imaging signal is important in FSEM because at high digitizing rates the number of quanta in the imaging signal available to determine the contrast level of a pixel in the final image may be quite small. For example, for a typical scan beam current of 1 nanoampere, only 31 electrons will strike the specimen in a digitizer sample time of 5 nanoseconds, corresponding to a digitizing rate of 200 MHz. This S/N ratio was shown to be a function of the brightness of the electron source; higher sources correlate with higher S/N ratios.

Although our FSEM device can be used to image any specimen in the SEM chamber undergoing dynamic motion, we also developed an in-situ (in the chamber) shock device to produce shock waves in solid specimens capable of moving or fracturing such specimens. This device is shown in FIG. 2 and is described in detail below and is illustrated in FIGS. 5 and 6.

BRIEF DESCRIPTION OF THE DRAWINGS

FIGS. 3a-3c shows the fast scanning scan coils of the invention.

Reference will now be made in detail to the present preferred embodiments of the invention, examples of which are illustrated in the accompanying drawings.

Figure 1:
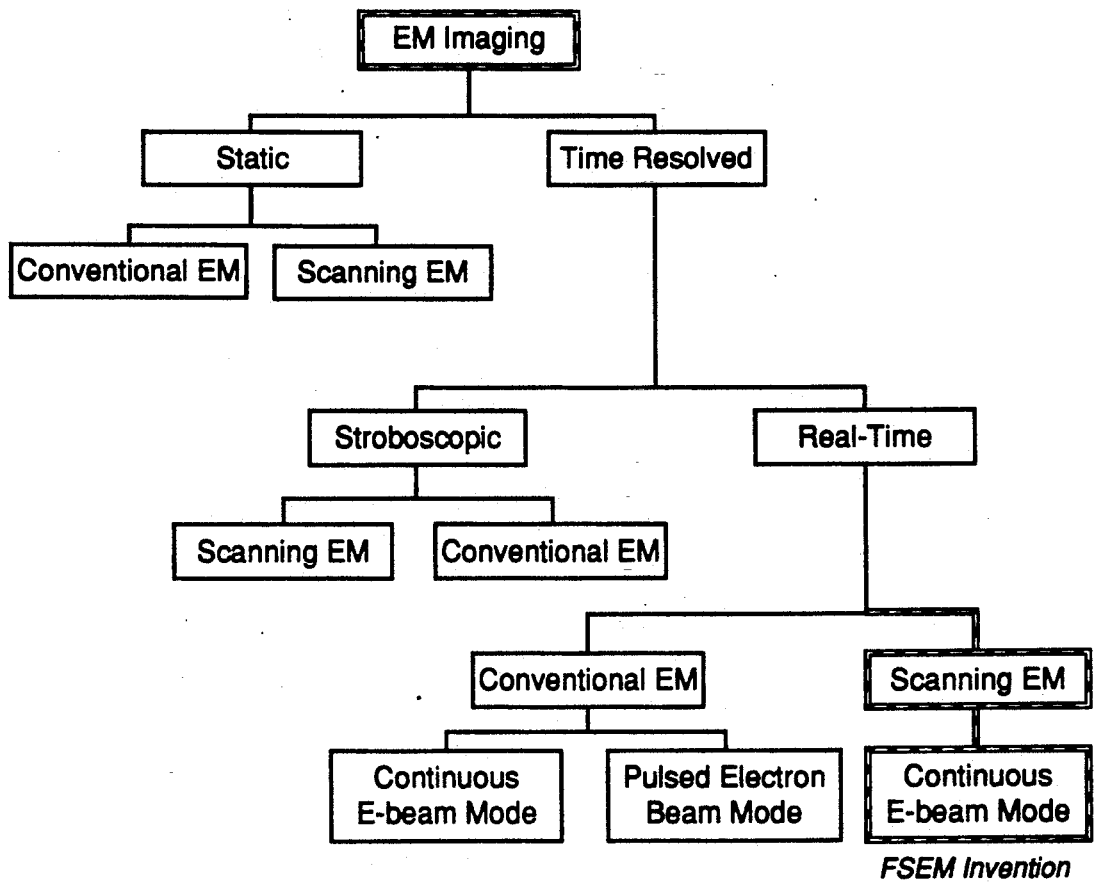
FIG. 1 shows an overview of the art of Electron Microscopy.
Figure 2:
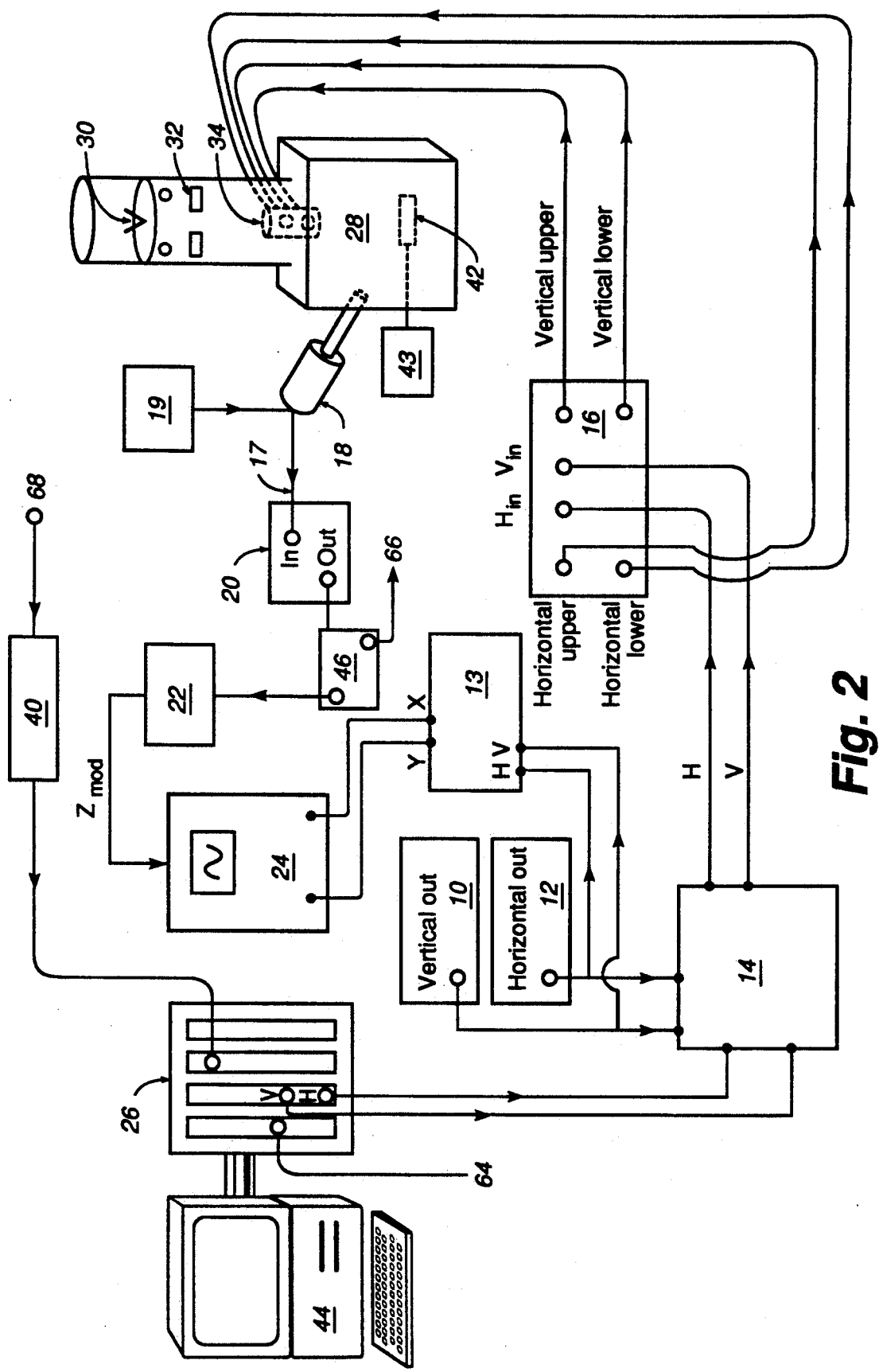
FIG. 2 shows a schematic of the FSEM system of the invention.

In FIGS. 2-5, identical or similar structure is identified by identical callouts. Turning now to the drawings, FIG. 2 shows a schematic of the FSEM system. This system is comprised of the following components: two analog signal generators, 10, 12, X-Y amplifier 13, a signal switcher, 14, a deflection-signal amplifier, 16, a secondary electron detector, 18, to which energy is supplied by high voltage supply 19, a preamplifier, 20, a video-amplifier, 22, an electron microscope chamber, 28, an electron source, 30, electromagnetic condenser lenses, 32, a set of magnetic deflection saddle-type scan coils, 34, a signal integrator, 40, a device to produce shock waves in a specimen, 42, a personal computer (PC), 44, and a switch, 46.

Our FSEM begins with an SX-40A ISI scanning electron microscope. It is equipped with a tungsten filament electron source, electromagnetic lenses, saddle-coil deflection coils, and an Everhart-Thornley (ET) photomultiplier secondary electron detector, typical of many SEMs on the market. In order to achieve the framing rates so far attained, three elements of the typical SEM were modified.

1. Scan Coils-To maintain linearity at the electron beams raster of the specimen the deflection coils were redesigned. Greatly lowering the inductance of the coils by reducing the number of turns, or windings of the saddle coils is necessary to achieve this reduction of inductance. Also an increase in the gauge of the wire used is needed to allow an increase of deflection current thereby compensating for the decrease of the magnetic deflecting field experienced with a reduction of the number of windings (see FIG. 3). In this redesign we took the previous saddle-type design and reduced the number of windings using a thicker wire. This has the effect of reducing the inductance characteristic of the previous design. When one tries to scan fast with high inductance coils, the current is a nonlinear function of time and the images received are distorted. Our modification of the existing coils allows us to enjoy linear current inputs so that our scanning can be conducted in a fast mode with reduced distortion. The high inductance levels of the previous designs limits the ability of the coils to deflect fast-enough to conduct our fast scanning activities.

Figure 3A:
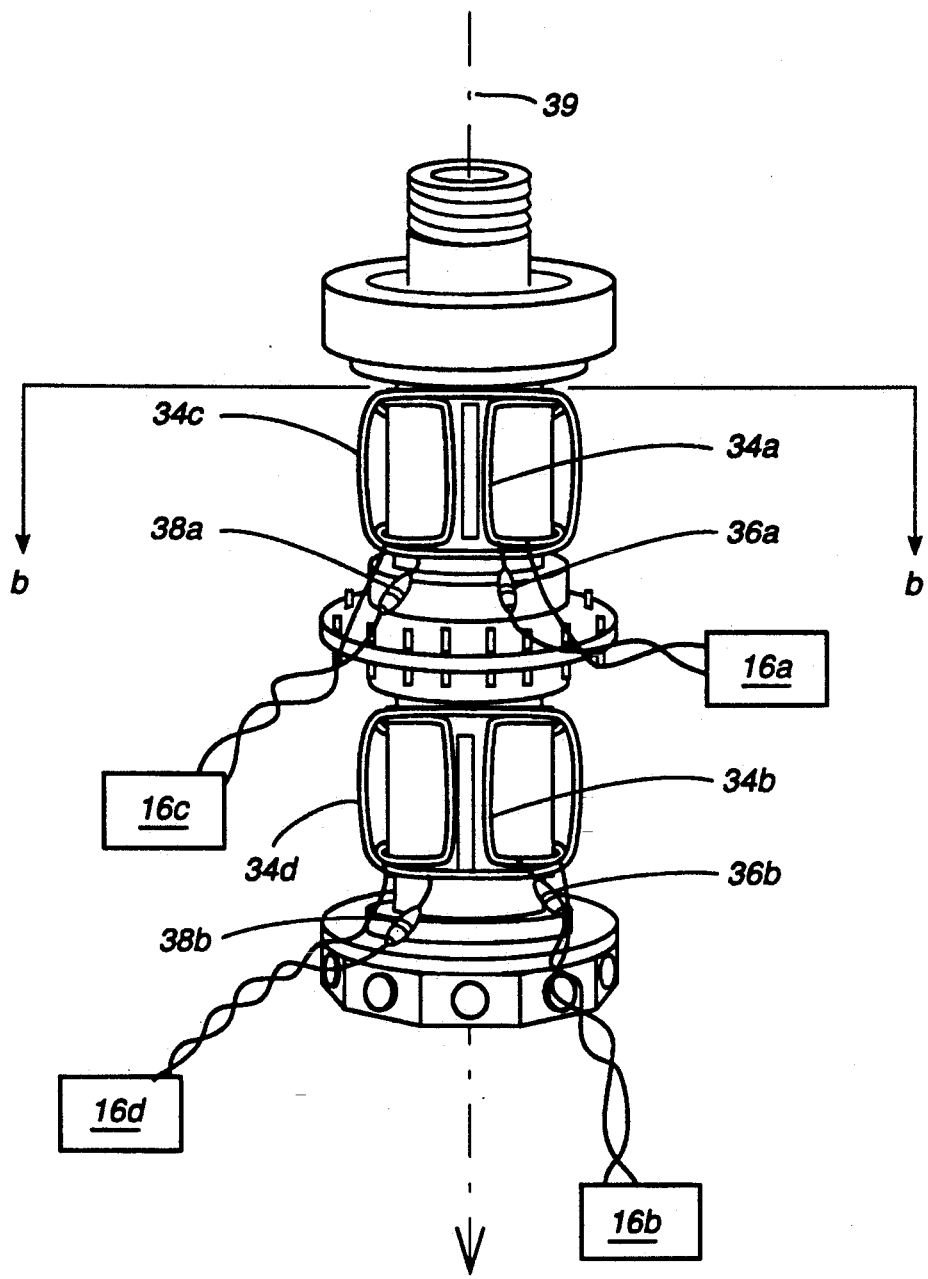

The existing scan coil assembly and drivers of the SX-40A introduced severe image distortion at even the slowest framing rate (47.4 Hz at 256 pixels X 256 pixels), so our efforts quickly focused on developing faster scan coils and drivers. We have used our fast deflection coils and drivers down to 1.6 microsecond horizontal line time and routinely operate at 10.25 microseconds horizontal line time. For comparison, TV-rate horizontal line time is typically 60 microseconds. A 1.6 microsecond horizontal line time means a framing rate of greater than 1 kHz would be possible at 256 pixels X 256 pixels if the scan generator could operate at higher pixel rates (presently limited to 25 MHz). Turning now to FIG. 3, FIG. 3a is a schematic representation of the saddle-type scan coils of the present invention. Vertical scan coils are identified as 34a and 34b, and are driven by scan coil drivers 16a and 16b through termination resistors 36a and 36b, respectively, while the horizontal scan coils are identified as 34c and 34d, and are driven by scan coil drivers 16c and 16d through termination resistors 38a and 38b, respectively. FIGS. 3b and 3c are schematic representations of cross section b—b of the upper scan coils, FIG. 3c illustrating only these coils. Upper and lower coils refer to the location of the coils along the electron beam axis, upper coils being located closer to the electron source 39. These coils differ from conventional SEM coils in the following sense. We lowered the inductance of the coils to allow for high-speed magnetic deflection. We chose the coil L/R (inductance to resistance ratio) to preserve isosceles triangle waveform (deflection current) for maximum value of digitizing rate. The inductance can be adjusted by reducing coil turns in the configuration in FIG. 3. The resistance of the coils can be adjusted by choice of coil wire material and diameter of the coil wire. As the ratio L/R becomes small, the B-field of connecting wires becomes an important restriction on the ratio. In redesigning our scan coils we adhered to the following design considerations. We wanted the resistance to equal the drive line impedance to insure that the coil driver sees a purely resistive load. We wanted to preserve the deflection B-field. We wanted to avoid exceeding the current and voltage capabilities of the coil driver. We wanted to control the coil capacitance and to preserve the lower coil inductance to upper coil inductance ratio. This places a constraint on the minimum number of turns. To preserve the large depth of field and other desirable SEM properties we wanted to stay with the double scan coil configuration shown in FIG. 3. The following design was built: the lower scan coils (both horizontal and vertical) had 7 turns of #25 gauge copper enamel wire; the vertical upper scan coils had 4 turns of #25 gauge copper enamel wire and the horizontal upper scan coils had 5 turns of #25 gauge copper enamel wire.

2. Modified Secondary Electron Detector-An increase in detection speed is needed to accept the greatly increased picture information being generated by faster scan rates. All elements of detection must be changed to facilitate this speed. A faster scintillator, photomultiplier tube (PMT), PMT base, and signal amplifiers are all necessary. All of the above were accomplished and provided in our FSEM design (see FIG. 4).

Figure 4:
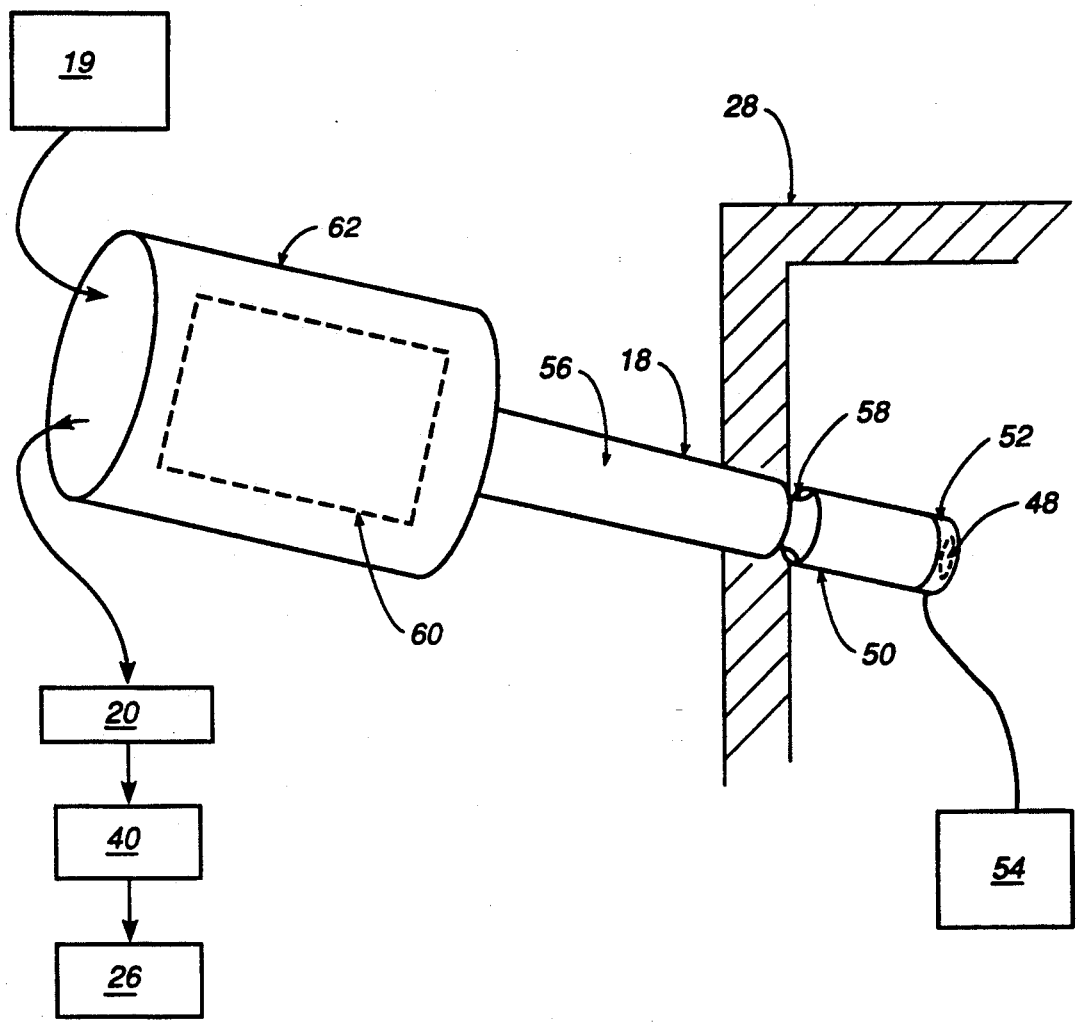
FIG. 4 shows the secondary electron detector used in the invention.

In FIG. 4, the scintillator, 48, is a commercial Ne111 type quenched plastic scintillator disk with 1 nanosecond full-width-at-half-maximum (FWHM) pulse width. It is fixed to a standard light tube, 50, using a metal cap, 52. An accelerating voltage is applied to metal cap 52 in order to attract secondary electrons by high voltage supply 54. The PMT tube, 56, used is a fast Hamamatsu R3082 with a 2.2 nanosecond rise-time. O-ring seal 58 permits a vacuum seal to chamber 28 to be maintained, and the high voltage required to operate the PMT is supplied by voltage supply 19. A high-speed, high-count rate PMT base, 60, was constructed using a circuit developed by C. R. Kerns, and described in "A High-Rate Phototube Base," IEEE Trans. Nucl. Sci., NS-24, 353 (1977). This PMT base was housed in a standard housing, 62. The PMT base response is at least 20 nanoseconds. Finally, an off-the-shelf high-speed broad-band preamplifier, 20, amplifies the pulses from the ET detector for analog-digital conversion. The careful combination of the above components produced representative pulses of the high-speed secondary electron output from a given sample which can then be digitally acquired.

3. High-Speed Data Acquisition and Scan-Coil Signal Generation-Finally, high speed coordinated data acquisition was necessary. At a scan rate of 381 frames/second and 256×256 pixels, a data or pixel rate of 25 MHz capability is needed. In addition, the data points (pixels) and scan position must be coordinated. This is accomplished using a lot a high speed LeCroy digitizer and a digital waveform generator which runs off the same clock as the LeCroy digitizer (FIG. 2, component H). A digital data acquisition system was assembled to provide scan signals synchronous with data acquisition. The data acquisition system itself is capable of 200 MHz pixel rate with total storage of 1 Mbyte which, for 256 pixels×128 pixels per frame, allows for total storage of 16 frames. This storage capability can easily be expanded to 32 frames with additional memory modules. The limiting factor in our pixel rate has been primarily the signal-to-noise ratio (S/N) available with the tungsten hairpin cathode we have been working with. We have obtained useable images at 25 MHz pixel rate. A second limitation has been the scan generation circuitry, limited to 25 MHz pixel rate at present. We have obtained analog acquired signals at an effective pixel rate of greater than 50 MHz which is close to the limit for the secondary electron detector we have developed.

The FSEM operation is as described for FIG. 2. An electron beam is produced by a tungsten filament 30 by the electron gun configuration of the SX-40A SEM. The beam is focused by electromagnetic lenses 32 of the standard SEM, onto the specimen in the specimen chamber 28. In order to view an image, an analog signal conversion is performed to facilitate focusing and specimen positioning. The magnetic deflection coils 34 are fed a saw-tooth scan signal from two analog signal generators 10, 12; one each for the vertical (10) and the horizontal (12) motions of the scanning beam (See also FIG. 3). These scan signals pass through a signal switcher 14 and into the high frequency operational deflection amplifiers 16. These amplifiers provided the necessary current to drive the scan coils 34. Signal electrons are then detected by the modified detector 18 and amplified by a Hewlett-Packard high frequency preamplifier 20. This signal goes either to a video amplifier 22 and to a 7704 Tektronix oscilloscope 24 for viewing by the operator, or it goes to a signal integrator 40 through terminals 66 and 68, and then to the LeCroy digitizer 26 when making a high-speed movie in the Fast-Scan mode. In addition, the sweep signal from the signal generators are fed to the scope 24 with the raster on the specimen in the SEM chamber 28. In the above description, a viewable image is obtained for focusing and picture optimization.

In FIG. 2, after the desired part of the specimen in the SEM chamber, 28, is viewed in real time on the cathode-ray-tube (CRT), 24, and the necessary adjustments (focusing, integrator, and acceleration voltage adjustment, filament alignment, etc.) are performed as in a normal SEM apparatus, fast scan data may be acquired. The integrator, 40, is a single resistance-capacitor (RC) analog type circuit with the time constant adjusted to maximize the image quality. Too long a time constant introduces too much analog-to-digital sampling error. First the FSEM software is enabled on the PC, 44, and the LeCroy, 26, is set up for data acquisition. The PC arms the LeCroy to acquire data. Pixel information is stored in the LeCroy's memory until it is accessed by the PC for image processing and viewing on a frame-by-frame basis. The sampling rate is set, pixel width and height are chosen, etc., and the LeCroy is "armed" and ready to acquire data. The detector signal is then sent by switch 46 to a signal integrator, 40, and to the LeCroy's analog inputs, 26. A trigger pulse is sent by means of a momentary push-button switch on the LeCroy unit, 64. This begins the data acquisition process and digital waveform generators 10, 12 then provide the deflection waveforms sent to scan coils 34. The trigger pulse is also used to [initiate the activation of the shock-device activate shock device 42 which is located within the SEM chamber to impart the desired motion to the specimen also located in SEM chamber 28. Typically, 16 frames of 256×128 pixels are acquired at a 25 MHz pixel rate (381 frames/second). Once the raw data from detector 18 are acquired they are sent to the PC, 44, hard disk to be processed and reviewed.

In FIG. 2, the term $Z_{mod}$ on the Tektronix 7704 oscilloscope, 24, is Z-modulation or intensity modulation. The secondary electron information from detector 18 is amplified and sent to the viewing CRT, 24, modulating the intensity of the CRT beam, thereby creating an image in real time. Also in FIG. 2, the secondary electron detection signal, 17, goes first to LeCroy inputs 66, 68, then to the integrator, 40, and to the LeCroy digitizer, 26.

Apparatus for Producing In-situ Shock to Specimens

Figure 5:
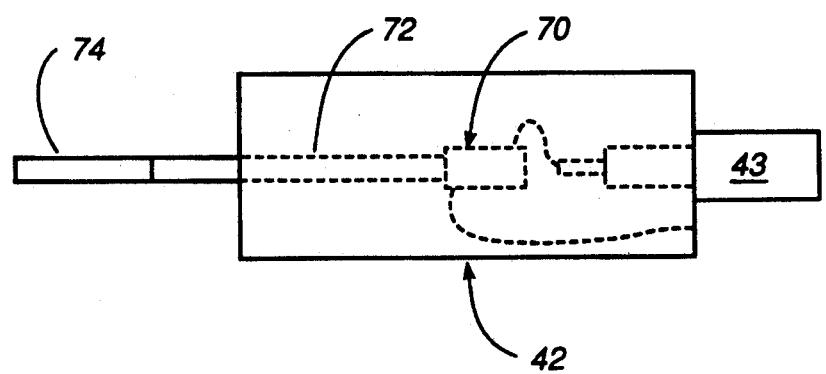
FIG. 5 shows an in-situ shock apparatus for use with the invention.

The in-situ shock device shown in FIG. 5 is a magnetically-induced stress wave generator for approximately 1-mm radius rod specimens, which allows dynamic loading in compression or tension in a single-ended mode (pressure acting initially from one end of a metallic rod surrounded on one end by a low-resistance electrical coil), and permits fracture to be localized within the SEM field of view and fracture scanning in real time. The device, 42, generates a one-dimensional compression or tension wave in a material through the generation of a magnetic pressure pulse at one end of a metallic rod. A pulsed-power circuit provides a pulse (MHV pulse input 43 in FIG. 5) to the device through a shielded wire feed-through that runs through the wall of the FSEM specimen chamber, 28. This pulse enters pressure coil 70 which induces an electromagnetic field around one end of brass rod 72. This field generates a one-dimensional dilatational wave which travels down the length of the brass rod and into the specimen (a rosin rod, 74, in FIG. 5). When the compression wave reaches the free end of the specimen, it reflects therefrom as a tension wave traveling in the opposite direction to the incoming compressional wave. If the reflected tension force exceeds the dynamic tensile strength of the specimen, 74, a fracture near the free end occurs. This fracture process is imaged by the FSEM apparatus of the present invention.

Figure 6:
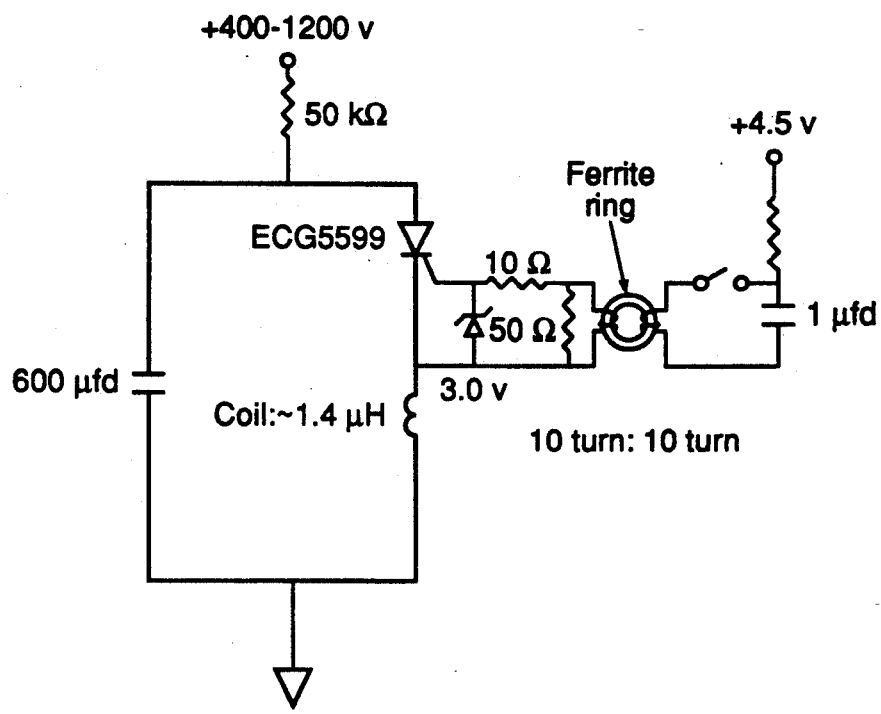
FIG. 6 is a schematic diagram of a pulse generator circuit to drive the shock apparatus shown in FIG. 5.

The pulsed-power circuit that delivers the pulse to this device is shown in the schematic diagram in FIG. 6. The generation of the pressure pulse in provided by a commercially available SCR. SCR triggering is simple and inexpensive and this method does not involve any kinetic impulse loading, which would disturb the specimen within or out of the FSEM field of view.

Having generally described the present invention, the following examples illustrate the operation thereof in more detail.

For any given experiment the beam voltage, deflection current, beam spot size, specimen working distance, detector placement and bias were adjusted to give the best digitized image. In general it was found necessary to increase final aperture diameter to obtain good signal-to-noise ratio (S/N) in the final image. This necessarily reduced the depth of focus in the image, restricting that portion of the field which is well-focused. Lower magnifications were desirable from a standpoint of understanding what was occurring in an in situ dynamic fracture experiment, for example. This was generally accomplished by lowering beam voltage and increasing deflection currents. At higher deflection currents the time allowed for imaging was restricted to reduce the possibility of over-heating the scan-coil assembly. For the experiments described below, test results and video movies were made in VHS format and placed on a videotape and submitted to the Air Force Office of Scientific Research (B.H. Fishbine, R.J. Macy, T.J. Ross, and M. L. Wang, "Development of a High-Imaging Speed SEM for Dynamically-Loaded Materials," Report to the Air Force Office of Scientific Research under the Small Business Innovation Research (SBIR) Program, Contract F49620-89-C-0013, Oct. 30, 1990).

i) Bead Blast Beads

To demonstrate the dynamic capabilities of the instrument, we placed some bead blast beads, small glass spheres used to clean and finish materials in a sandblast-like process, onto a piezoelectric transducer. The transducer was excited by a waveform to cause the spheres to move rapidly enough to provide an interesting digital movie at 381 Hz framing rate. We believe the movie demonstrates the soundness of our approach to dynamic microscopy. To increase S/N, the final SEM column aperture was increased to a minimum of 1 millimeter. This reduces depth of focus; a brighter source would allow for comparable S/N but increased depth of focus, hence increased image sharpness.

ii) Fuse Blow

Our next experiment was to attempt to image the opening of a small fuse. After experimenting with such fuses we found that they could be made to open in tens of milliseconds after applying a high-current pulse to them. At 381 Hz, the time per frame is 2.62 milliseconds.

After applying the current pulse, the image quality would decrease dramatically. A few frames later the fuse would re-appear. Then the image would be washed out completely for several frames. After washout the fuse would be visible again. We believe that what happens is that after current is applied, the fuse heats up enough to outgas absorbed gases but not enough to melt and open. Outgassing means that near the fuse the primary beam electrons may be scattered somewhat and secondaries may be scattered so much that image quality is greatly degraded. We believe the image re-appears after outgassing ends. We believe the second wash-out was caused by the fuse wire heating to incandescence, whose light swamps the PMT.

To prove this we spent some time improving the light-shielding around the PMT and around the fuse. This essentially eliminated the second washout problem.

We also speculated that when the fuse is heated to incandescence it becomes a thermionic electron source that swamps the secondary electron signal. To test this idea, we took a two-volt incandescent bulb and removed the glass envelope. The bulb was then placed inside the specimen chamber where the fuse had been and current passed through sufficient to make the filament glow brightly. This was with light shielding of the PMT and filament in place. The image of the filament of the CRT screen was not affected in these experiments, thus the thermionic contribution is believed to be negligible.

After eliminating the light problem, we found that though the fuse takes tens of milliseconds to open, the visual process of the fuse opening takes less than 2.62 milliseconds. That is, with the present limited image sharpness available with our tungsten cathode, we see no evidence of melting or other changes in the fuse surface until from one frame to the next, a small section of fuse disappears.

Microscope operating parameters for this data, taken on May 23, 1990, were as follows. Beam voltage—3 kV. Working distance—65 mm. Tilt—0°. No final aperture ($\geq 1$ mm diameter). Specimen current—55 nA (Maximum spot size). Pixel rate—25 MHz. PMT voltage——1300 volts. Everhart-Thornley collection bias—+200 volts.

At this pixel rate there were $\sim 13750$ primary electrons/pixel (assuming specimen current $\sim$ probe current). Assuming $f\delta = 0.1$, $S/N \sim 37$, where f is detector collection and detection efficiency and $\delta$ is specimen secondary electron yield. (S/N, of course, was drastically reduced when f is drastically reduced by secondary scattering through outgassing gases.) The primary beam semi-convergence angle was greater than 7.69 milliradians.

iii) In Situ Dynamically-Loaded Fracture

The first in situ fracture results with a simultaneous SEM scan were obtained with our single-ended compression shock loading device and fracture in free-end reflected tension with the compression pulse generated in a 1.03 millimeter radius brass rod attached to rosin rod of approximately the same diameter. At higher currents the rosin was found to fracture 1) in a two-thirds/one-third length fraction for rosin rod of 2 centimeter length and a brass rod length of 3 centimeters, and 2) at the brass/rosin interface. As circuit inductance increased as power cable length was increased and the high-voltage coaxial feed-through at the SEM specimen chamber added inductance, the peak pressure was reduced, so that fracture only occurred at the brass/rosin interface. However, i did so reliably and so was chosen for first in situ fracture scans.

The first problem in making this measurement was to shield the plastic from the electromagnetic pulse (emp) environment. In the first tests, at early times there was noise on the transducer signal, but by the time the pressure pulse arrived at the plastic the results looked plausible, although amplitudes were an order of magnitude low and there was much more going on than one would think by examining the magnetic pressure pulse.

The in-situ shock device was built and tested in a single-ended compression version with a ballistic pendulum to a peak pressure of 3,300 psi with a pulse-width of 1.23 microseconds at a capacitor charge voltage of 10 kV. Another version of the device was tested to a capacitor charge voltage of 20 kV, corresponding to a peak pressure of 13,200 psi.

Once we demonstrated that rosin could be fractured in tension with the single-ended compression version of the shock wave device outside the FSEM chamber, we attempted to image fracture dynamically inside the FSEM using this fracture method.

The first concern was that the electromagnetic-pulse (emp) generated by the shock wave device might damage the electronics in the data acquisition system, the detector system or in the FSEM itself. Our second concern was that even if no electronics were damaged, it might take too much time for the electronics to recover from the emp to obtain a decent scan.

Our original concept was to place the magnetically-induced stress wave device capacitor bank and switch in an electromagnetically shielded box constructed from copper or brass screen or sheet. We also planned to similarly shield the Patco pulse generator, which produces a 50 kV amplitude pulse in a few nanoseconds. (This pulse generator is notoriously noisy mainly because its output pulse is seldom terminated in order to get maximum pulse amplitude and minimum pulse risetime for good triggering.) However, we soon decided to place both these components, plus the capacitor bank charge supply and associated equipment entirely in a double-shielded electromagnetic enclosure. Feedthroughs into the FSEM chamber were then provided for spark gap switch gas flow, capacitor bank voltage monitor, pulse trigger input, pulse trigger sync out, pressure coil current monitor and a coaxial transmission line feed from the capacitor bank to the pressure coil.

This set-up worked well in initial tests in which a 2 foot length of RG59 cable connected from the double-shielded enclosure to a small Pomona box with an MHV feed-through and the pressure coil, as shown schematically in FIG. 5. The box was mounted on the FSEM specimen stage for the digital movies. Rosin was reliably fractured at 10 kV charge with this set-up. It fractured at the brass/rosin interface.

Microscope operating parameters for this test were as follows. Beam voltage—1 kV. Working distance—66 mm. Tilt—+0.50°. No final aperture. PMT voltage——1490 volts. Everhart-Thornley collection bias—+200 volts. The primary beam semi-convergence angle was ≧7.58 milliradians.

Summary of Reduction to Practice

In summary, we have obtained secondary electron images with a modified scanning electron microscope at resolutions of less than 100 nanometers and 381 Hz framing rate. This is an order of magnitude increase in framing rate over that previously available in SEM, while retaining SEM advantages of high spatial resolution, large depth of focus, and voltage and magnetic contrast imaging with the secondary electron signal. We believe that appropriate components may permit framing rate of 100 kHz–1 MHz, with reduced pixel resolution.

The concept of using a high-speed scanning electron microscope (SEM) to observe real-time microstructural response of dynamically loaded structural materials was verified experimentally at a maximum framing rate of 381 Hz (256 horizontal pixels×128 vertical pixels), about an order of magnitude higher than previously possible with conventional SEM's. This experimental accomplishment proved the soundness of several key concepts:

That a tungsten hairpin cathode is bright enough to obtain useful digital images at the framing rate listed above, That a secondary electron detector can be built and operated at high enough count rates to obtain such images, That the scan coil assembly standard on an ISI SX-40A SEM can be replaced to allow imaging at such rates with spatial resolution approaching 100 nanometers, That signal acquisition and scan generation can be synchronized to obtain a succession of well-defined frames in a "movie" format at pixel rates far in excess of conventional TV-rate SEM video bandwidths, and That a magnetically-induced stress wave device can be used to obtain dynamic fracture within the SEM chamber and field of view, with scanning timed to coincide with fracture.

These developments should allow a variety of new SEM dynamic microscopy studies, ranging from microstructural material response to dynamic loading, to studies of flux creep in high $T_c$ superconductors, at spatial resolutions and time-scales not possible before.

And so, the scope of the invention should be determined by the claims and their legal equivalents, instead of the examples given here.

Potential Applications of the FSEM

With the FSEM capabilities discussed above, a variety of dynamic microscopic studies become possible. Chief among these is microstructural response of structural materials to transient loads, such as mechanical, thermal and magnetic loads. The Table below shows the technology areas that we have reviewed over the last 2 years that could benefit from the utility of our FSEM device. Certain modifications, such as thermal stages or a gaseous environment, to the stages would be necessary, but the FSEM technology could be readily adapted to these situations.

Table

Potential Applications of FSEM monolayer studies (Langmuir-Blodgett)—may require "wet" SEM
recrystallization of silicon films and semiconductors
real-time dynamic fracture
In situ SEM- or microprobe-observed fracture
TEM video microscopy (TV-rate)

solid phase transitions (see high $T_c$ superconductor listings below)
atomic motion within crystals
Pulsed electron microscopy—non-scanned (~25 ns/frame)
TEM studies of laser-pulse-induced processes
reflection electron microscope surface studies
High $T_C$ superconductor studies
phase transitions during fabrication—SEM
flux creep, magnetic contrast imaging—SEM
flux creep, decoration imaging—SEM
Domain growth/transition of polymers
Integrated circuit inspection and metrology
E-beam testing of integrated circuits (strobed voltage contrast in SEM)
E-beam specimen damage reduction

We claim:

1. An apparatus for observing the real-time microstructural response of dynamically-loaded materials, said apparatus comprising in combination:
   a. a high-speed continuous-scanning electron microscope having a spatial resolution of less than 100 nm in the submillisecond time region for interrogating the material under investigation; and
   b. means for providing aperiodic tension and compression shock waves to the material.

2. The apparatus as described in claim 1, wherein said means for providing tension and compression shock waves comprises a low-resistance electrical coil surrounding a metallic rod, and means for applying a rapid electrical pulse to said coil.

3. The apparatus as described in claim 1, wherein said continuous-scanning electron microscope and said means for providing tension and compression shock waves are synchronized, whereby a succession of well-defined frames showing of the microstructural response of the material under observation is obtained.

4. The apparatus as described in claim 1, wherein said high-speed continuous-scanning electron microscope comprises low-inductance electron beam magnetic deflection coils having nanosecond rise-times adapted for receiving rapidly varying current, whereby a sweep rate of less than 10 $\mu$s per horizontal line over the material under observation is achieved.

5. The apparatus as described in claim 4, wherein said high-speed continuous-scanning electron microscope comprises a high-speed secondary electron detector capable of accepting the increased rate of generated secondary electrons resulting from the faster scan rates.

6. The apparatus as described in claim 5, wherein said high-speed continuous-scanning electron microscope comprises a digital scan generator for generating a deflection waveform in said low-inductance electron beam magnetic deflection coils which is synchronized with said high-speed secondary electron detector such that real-time data acquisition capability is achieved.

7. The apparatus as described in claim 2, wherein said metallic rod is a copper rod.

8. A real-time, continuous scanning electron microscope comprising electron beam generation means, electron beam focusing means, electron beam deflection means for directing the electron beam onto a target, secondary electron detection means, and means for processing signals generated by said secondary electron detection means, the improvement therein comprising low-inductance electron beam deflection coils having nanosecond rise-time, and means for providing rapidly varying current to said low-inductance coils in order to enable a sample to be scanned at a rate faster than 10 $\mu$s/horizontal line.

9. The apparatus as described in claim 8, wherein the inductance and resistance of said electron beam deflection coils are chosen such that a sawtooth sweep waveform is preserved for scan rates faster than 10 $\mu$s/horizontal line sweep by selecting the number of coil turns and the coil wire material and diameter, respectively.

10. The apparatus as described in claim 8, wherein said secondary electron detection means comprises a high-speed secondary electron detector capable of accepting the increased rate of generated secondary electrons resulting from the faster scan rates.

11. The apparatus as described in claim 10, wherein said means for providing rapidly varying current to said low-inductance coils comprises a digital scan generator which is synchronized with said high-speed secondary electron detector such that real-time data acquisition capability is achieved.

* * * * *